(12) United States Patent
Paruchuri et al.

(10) Patent No.: US 11,237,008 B2
(45) Date of Patent: Feb. 1, 2022

(54) SYSTEM AND METHOD FOR CONTROLLING VEHICULAR POLLUTION CONCENTRATION AND PROVIDING MAXIMUM TRAFFIC FLOW THROUGHPUT

(71) Applicant: INTERNATIONAL INSTITUTE OF INFORMATION TECHNOLOGY, HYDERABAD, Hyderabad (IN)

(72) Inventors: Praveen Paruchuri, Hyderabad (IN); Sreeja Kamishetty, Hyderabad (IN); Soumya Vadlamannati, Hyderabad (IN)

(73) Assignee: International Institute of Information Technology, Hyderabad, Hyderabad (IN)

( * ) Notice: Subject to any disclaimer, the term of this patent is extended or adjusted under 35 U.S.C. 154(b) by 102 days.

(21) Appl. No.: 16/724,322

(22) Filed: Dec. 22, 2019

(65) Prior Publication Data

US 2020/0200555 A1    Jun. 25, 2020

(51) Int. Cl.
*G01C 21/34* (2006.01)
*G01N 33/00* (2006.01)
*B60W 40/02* (2006.01)
*G08G 1/01* (2006.01)

(52) U.S. Cl.
CPC ......... *G01C 21/3469* (2013.01); *B60W 40/02* (2013.01); *G01N 33/0004* (2013.01); *G08G 1/0145* (2013.01)

(58) Field of Classification Search
CPC ... G01C 21/3469; G01C 21/34; B60W 40/02; G01N 33/0004; G08G 1/0145
See application file for complete search history.

(56) References Cited

U.S. PATENT DOCUMENTS

2006/0241855 A1* 10/2006 Joe .................. G01C 21/34
                                                     701/533

* cited by examiner

*Primary Examiner* — Tyler J Lee
*Assistant Examiner* — Yufeng Zhang (57) ABSTRACT

A method for providing maximum traffic flow throughput and controlling vehicular pollution concentration is provided. The method includes (i) processing a source location and a destination location obtained from a user device associated with a user to determine at least one possible route to reach the destination location from the source location, (ii) determining at least one maximum flow route that includes at least one edge with an edge capacity from the at least one possible route, (iii) determining maximum traffic flow capacity for the at least one maximum flow route, (iv) determining active traffic flow routes by comparing continuously if shared or common edges of a plurality of route solutions is less than or equal to a pre-defined limit and (v) partitioning the maximum traffic flow capacity for the active traffic flow routes and permuting each partition of the maximum traffic flow capacity for the active traffic flow routes.

11 Claims, 8 Drawing Sheets

SYSTEM AND METHOD FOR CONTROLLING VEHICULAR POLLUTION CONCENTRATION AND PROVIDING MAXIMUM TRAFFIC FLOW THROUGHPUT

CROSS-REFERENCE TO PRIOR FILED PATENT APPLICATIONS

This application claims priority from the Indian provisional application no. 201841048754 filed on Dec. 22, 2018, which is herein incorporated by reference.

BACKGROUND

Technical Field

The embodiments herein generally relate to vehicles-pollution mitigation strategy, more particularly, to a computationally implemented system and method for reducing concentration of vehicular pollution by enabling specific patterns of vehicular flow at different times and providing maximum traffic flow throughput.

Description of the Related Art

In modern society, engine vehicles are one of the very important means of transportation. Such engine vehicles include two-wheelers, three-wheelers, and four-wheelers. Recently, air pollution in the center of a city or on the main roads is on the rise due to the increase in individual vehicles. Most of the individual vehicle drivers in order to reach their destination follow a few common and known routes. The selection of common routes for reaching the destination result's in flash crowding in some specific regions and further leads to a rise in concentration of air pollution along the routes in such regions. One of the major reasons for most individuals to take up these common routes regularly and repeatedly is the preference for the shortest and the known routes while traveling from source to the destination.

Since most of the vehicle drivers prefer traveling through the known routes it results in an increase in vehicular concentration on such routes. This increase in vehicular concentration further increases the pollution concentration on such routes and hence creates an imbalanced and unequal pollution distribution condition across the city. The uneven distribution of air pollution causes a burden over the natural amenities surrounding such a region and is also harmful to the people traveling through or is residing nearby.

At present, nations and local governments operate air pollution monitoring stations in order to monitor the air pollution levels. The air pollution monitoring stations are fixed and may be classified into an urban air pollution monitoring station and a roadside air pollution monitoring station. The roadside air pollution monitoring stations located at crossroads provide pollution monitoring systems to monitor pollution concentration across the region.

Many conventional pollution monitoring and traffic guidance systems have been designed in the past. One of the techniques employing Journey planning in public transportation networks has been disclosed in the prior art.

The above-mentioned United States patent publication discloses "Optimum journeys in public transportation networks". The determination of Pareto optimal journeys from one stop to another stop in a public transportation network uses the criteria travel time and minimum transfers. A technique for bi-criteria journey planning using the aforementioned criteria in public transportation networks operates in rounds (K rounds at most), where after round k ($k \leq K$), arrival times are computed for the stops that can be reached with up to k trips. The abovementioned prior art though is provided for determining optimum journeys in public transportation networks but fails to address flash crowding and unequal pollution distribution problem. Also, the mentioned above prior art lacks a k-optimality filtering feature for the multiple PMFA outputs.

Accordingly, there remains a need for a system and method for reducing the concentration of vehicular pollution by enabling specific patterns of vehicular flow at different times and providing a maximum traffic flow throughput.

SUMMARY

In view of the foregoing, an embodiment herein provides a method for providing maximum traffic flow throughput and controlling vehicular pollution concentration. The method includes the steps of (i) processing a source location and a destination location obtained from a user device associated with a user to determine at least one possible route to reach the destination location from the source location, the at least one possible route has at least one edge with an edge capacity (ii) determining at least one maximum flow route solution that includes the at least one possible route (iii) determining maximum traffic flow capacity for the at least one maximum flow route solution (iv) determining one or more active traffic flow route solutions by identifying all possible routes from the source location to the destination location (v) partitioning the maximum traffic flow capacity for one or more active traffic flow route solutions and permutes each partition of the maximum traffic flow capacity to identify valid flows for one or more active traffic flow route solutions (vi) comparing each permutation of partition of the maximum traffic flow capacity for the one or more active traffic flow route solutions and appending a validated traffic flow route solution from the source location to the destination location to a database (vii) determining one or more validated traffic flow route solutions by comparing continuously if shared or common edges of one or more route solutions is less than or equal to a pre-defined limit; and (viii) generating one or more distributions of traffic flow across the active traffic flow route solutions and controlling concentration of vehicular pollution in a specific route by allowing one or more vehicles on different days.

In some embodiments, at least one possible route solution is determined by (i) identifying at least one edge with a pre-defined capacity that is near to the source location and (ii) constructing a route from the source location to the destination location with the at least one edge.

In some embodiments, the maximum traffic flow capacity determined for at least one edge defines the plurality of vehicles acceptable in the at least one edge which determines a pollution level for the at least one edge.

In some embodiments, the method further includes measuring shared number of edges or shared distance between the source location and the destination location.

In some embodiments, the edge capacity is a value that defines the traffic flow capacity of each edge.

In one aspect, one or more non-transitory computer readable storage medium storing the one or more sequence of instructions, which when executed by a processor, further causes a method for providing maximum traffic flow throughput and controlling vehicular pollution concentration, the method includes (i) processing a source location and a destination location obtained from a user device associated with a user to determine at least one possible route to reach the destination location from the source location, the at least one possible route has at least one edge with an edge capacity (ii) determining at least one maximum flow route solution that includes the at least one possible route (iii) determining maximum traffic flow capacity for the at least one maximum flow route solution (iv) determining one or more active traffic flow route solutions by identifying all possible routes from the source location to the destination location (v) partitioning the maximum traffic flow capacity for one or more active traffic flow route solutions and permutes each partition of the maximum traffic flow capacity to identify valid flows for one or more active traffic flow route solutions (vi) comparing each permutation of partition of the maximum traffic flow capacity for the one or more active traffic flow route solutions and appending a validated traffic flow route solution from the source location to the destination location to a database (vii) determining one or more validated traffic flow route solutions by comparing continuously if shared or common edges of one or more route solutions is less than or equal to a pre-defined limit; and (viii) generating one or more distributions of traffic flow across the active traffic flow route solutions and controlling concentration of vehicular pollution in a specific route by allowing one or more vehicles on different days.

In some embodiments, the method further includes measuring shared number of edges or shared distance between the source location and the destination location using the common or shared edges between one or more route solutions.

In another aspect, a system for providing maximum traffic flow throughput and controlling vehicular pollution concentration is provided. The system includes a server that is communicatively coupled with a user device associated with a user. The server includes a memory that stores a set of instructions and a processor that executes the set of instructions and is configured to (i) processing a source location and a destination location obtained from a user device associated with a user to determine at least one possible route to reach the destination location from the source location, the at least one possible route has at least one edge with an edge capacity (ii) determining at least one maximum flow route solution that includes the at least one possible route (iii) determining maximum traffic flow capacity for the at least one maximum flow route solution (iv) determining one or more active traffic flow route solutions by identifying all possible routes from the source location to the destination location (v) partitioning the maximum traffic flow capacity for one or more active traffic flow route solutions and permutes each partition of the maximum traffic flow capacity to identify valid flows for one or more active traffic flow route solutions (vi) comparing each permutation of partition of the maximum traffic flow capacity for the one or more active traffic flow route solutions and appending a validated traffic flow route solution from the source location to the destination location to a database (vii) determining one or more validated traffic flow route solutions by comparing continuously if shared or common edges of one or more route solutions is less than or equal to a pre-defined limit; and (viii) generating one or more distributions of traffic flow across the active traffic flow route solutions and controlling concentration of vehicular pollution in a specific route by allowing one or more vehicles on different days.

In some embodiments, the at least one possible route solution is determined by (i) identifying at least one edge with a pre-defined capacity that is near to the source location, (ii) constructing a route from the source location to the destination location with the at least one edge.

In some embodiments, the maximum traffic flow capacity determined for at least one edge defines one or more vehicles acceptable in the at least one edge which determines a pollution level for the at least one edge.

In some embodiments, the processor configured to measure shared number of edges or shared distance between the source location and the destination location.

In some embodiments, the edge capacity is a value that defines the traffic flow capacity of each edge.

The system is used for reducing and equally distributing the concentration of vehicular pollution caused due to flash crowding in specific routes. The system generates route solutions for reaching a destination from the source and suggests these route solutions to the air pollution monitoring station. In some embodiments, an air pollution monitoring station that is connected to the user device over a network receives input of various route solutions and uses these route solutions on different days to distribute the pollution more uniformly with the aim of reducing the concentration of pollution in specific areas.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a system and method for reducing and distributing the concentration of vehicular pollution caused due to flash crowding in specific routes. The embodiments herein achieve this by proposing a system that reduces the concentration of vehicular pollution by allowing vehicles in different routes and at different times. Referring now to the drawings, and more particularly to FIGS. 1 through 7, where similar reference characters denote corresponding features consistently throughout the figures, there are shown preferred embodiments.

Figure 1:
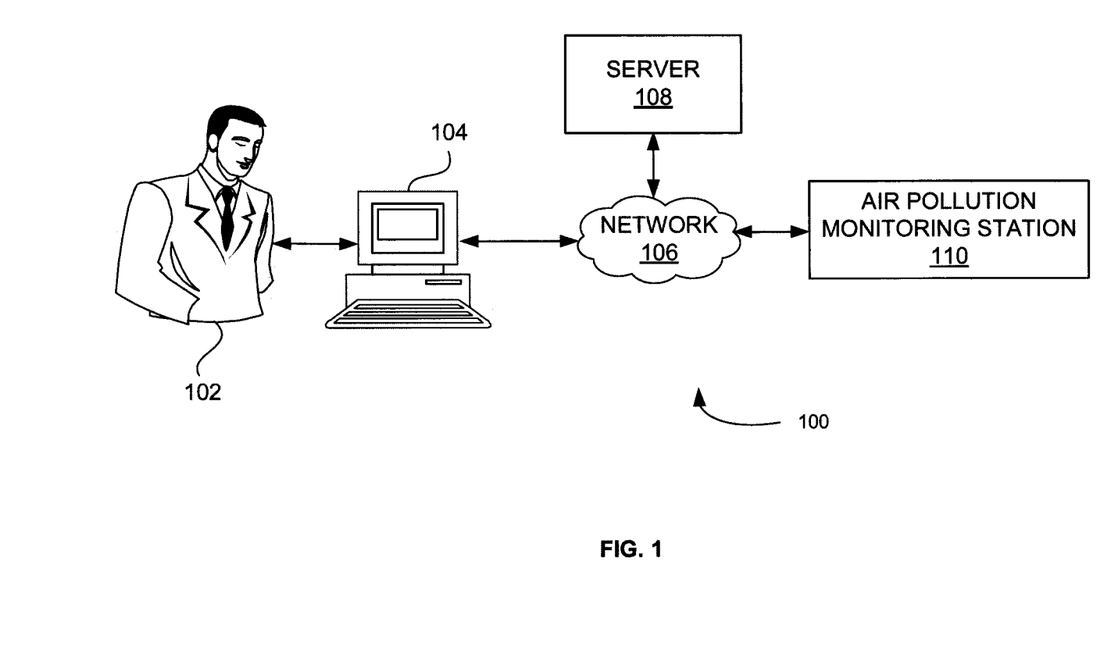
FIG. 1 is a block diagram that illustrates a system view of reducing concentration of vehicular pollution by enabling specific patterns of vehicular flow at different times and providing a maximum traffic flow throughput according to some embodiments herein.

FIG. 1 is a block diagram 100 that illustrates a system view of reducing the concentration of vehicular pollution by enabling specific patterns of vehicular flow at different times and providing a maximum traffic flow throughput according to some embodiments herein. The block diagram 100 includes a user 102, a user device 104, a network 106, a server 108 and an air pollution monitoring station 110. In some embodiments, the server 108 enables to reduce the concentration of vehicular pollution by enabling specific patterns of the vehicular flow at different times through different routes and guarantees a max traffic flow throughput. The air pollution monitoring station 110 may obtain input of various route solutions and communicates the input of various route solutions to the user device 104 through the network 106. The user device 104 obtains source (S1) location and destination (D1) location from the user 102.

In some embodiments, the user device 104 may be a mobile phone, a kindle, a PDA (Personal Digital Assistant), a tablet, a music player, a computer, an electronic notebook or a smartphone. The server 108 receives and processes the source (S1) location and the destination (D1) location information from the user device 104 through the network 106 to determine one or more possible routes from the source (S1) location to the destination (D1) location.

In some embodiments, the network 106 is a wired network. In some embodiments, the network 106 is a wireless network. In some embodiments, the network 106 is a combination of a wired network and a wireless network. In some embodiments, the network 106 is the Internet.

The server 108 determines at least one maximum flow route that includes at least one edge with an edge capacity from the at least one possible route. In some embodiments, each route is a combination of multiple roads/edges and intersections. In some embodiments, each edge is assigned by an edge capacity. The edge capacity is a value that defines the traffic flow capacity of each edge. In some embodiments, the server 108 selects any random route solution from available various route solutions stored in a database. In some embodiments, a route solution is selected for comparing s selected route solution obtained from a selection module with other route solutions stored in the database. In some embodiments, communicates an information about the at least one maximum flow route to the user device 104. In some embodiments, the server 108 continuously compares the selected route solution until all the route solutions are compared with the picked-up route solution. In some embodiments, the picked-up route solution is a part of the route solutions stored in the database. In some embodiments, the user device 104 stores the information about the at least one maximum flow route in a user device database.

The server 108 determines maximum traffic flow for the at least one maximum flow route. In some embodiments, the server 108 determines maximum traffic flow using a Ford Fulkerson algorithm (FFA). In some embodiments, each edge within the route includes a pre-defined pollution level set by the server 108. The pollution level for the edges across the route may decide a number of vehicles that are passed through the edges which further defines the traffic flow capacity of the edges. In some embodiments, the maximum traffic flow is defined as the maximum allowable traffic flow through each edge and across each route. The server 108 may provides an output that indicates the common edges between two routes. In some embodiments, the server 108 includes a pre-defined limit of common or shared edges between the two routes which implies that the shared edges between the two routes that include the pre-defined limit. The server 108 checks the route solutions that exceed the pre-defined limit of common edges when the number of common edges with the picked-up route solution is computed. The server 108 determines one or more active traffic flow routes by comparing continuously if the shared or common edges of the route solutions are less than or equal to the pre-defined limit. In some embodiments, the route solutions that exceed the pre-defined limit are considered as non-active traffic flow routes.

The server 108 partitions the maximum traffic flow capacity for the one or more active traffic flow routes. The server 108 permutes each partition of the maximum traffic flow capacity for the one or more active traffic flow routes. In some embodiments, the maximum traffic flow capacity is minimum when compared to each edge capacity of each edge.

The server 108 compares each permutation of partition of the maximum traffic flow capacity for the one or more active traffic flow routes and appending a validated traffic flow route from the source location to the destination location to the database. The server 108 generates one or more distributions of traffic flow across the one or more active traffic flow routes and controls concentration of vehicular pollution in a specific route by allowing one or more vehicles on different days.

In some embodiments, the server 108 determines at least one possible route solution by (i) identifying at least one edge with a pre-defined capacity that is near to the source location and (ii) constructing a route from the source location to the destination location with the at least one edge.

Figure 2:
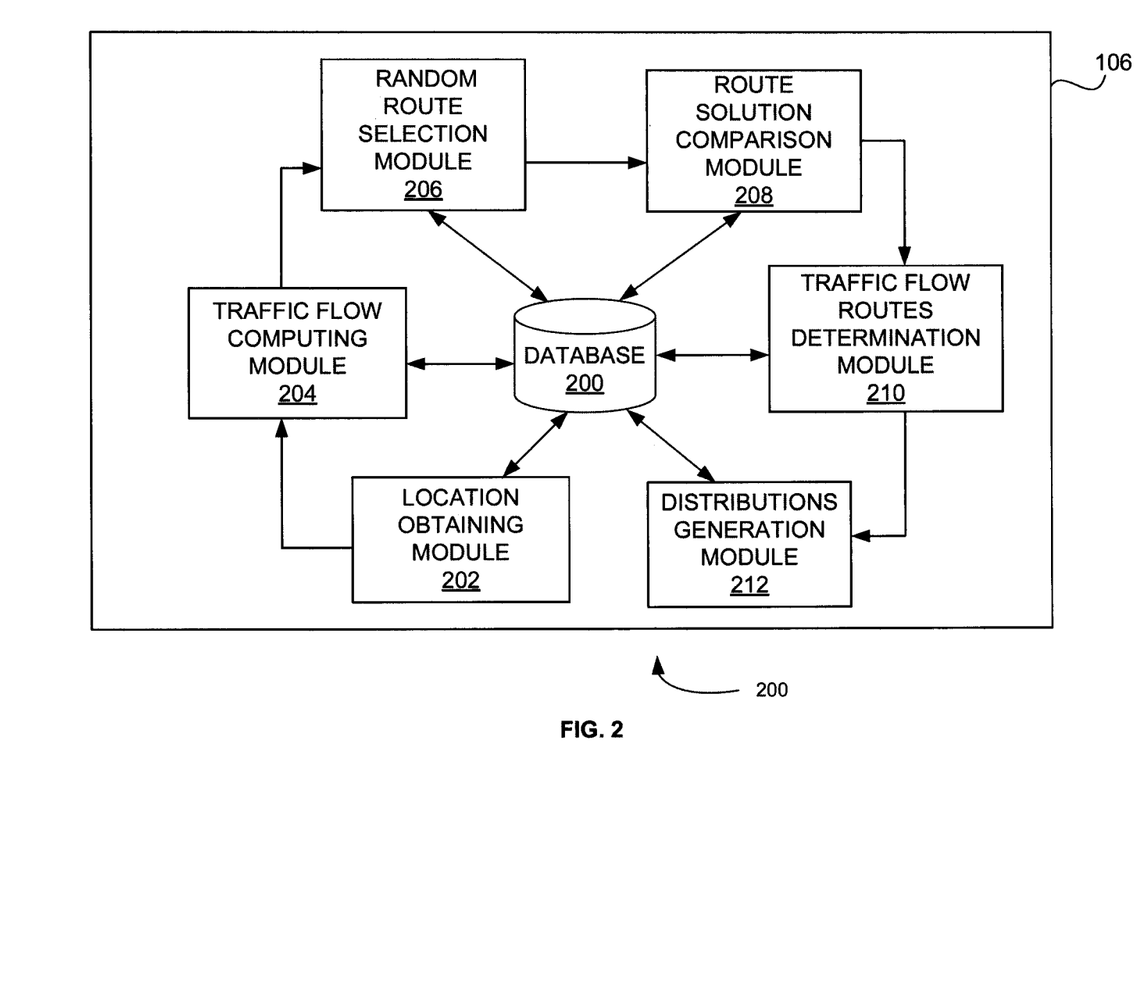
FIG. 2 is a block diagram of a server of FIG. 1 according to some embodiments herein.

FIG. 2 is a block diagram of the server 108 of FIG. 1 according to some embodiments herein. The server 108 includes the database 200, a location obtaining module 202, a traffic flow computing module 204, a random route selection module 206, a route solution comparison module 208, a traffic flow routes determination module 210 and a distributions generation module 212. The location obtaining module 202 obtains the information that includes the source (S1) location and destination (D1) location information from the user 102. The database 200 stores the gathered information that includes the source (S1) location and destination (D1) location information that is provided by the user 102. The traffic flow computing module 204 computes maximum traffic flow possible from the source to the sink using the standard ford Fulkerson algorithm. The traffic flow computing module 204 identifies the set of route solutions that includes the maximum flow capacity. The traffic flow computing module 204 may compute the maximum traffic flow capacity for each route solution composed of the one or more edges.

The random route selection module 206 selects any random route solution from the various available route solutions stored in the database 200. The route solution comparison module 208 compares the selected route solution obtained from the random route selection module 206 with other route solutions stored in the database 200 to determine the shared or common edges (k) between the route solutions. The traffic flow routes determination module 210 determines whether the route solutions having the shared or common edges (k) within a predefined limit by analyzing the route solutions. The traffic flow routes determination module 210 determines at least one of (i) the non-active traffic flow routes when the shared or common edges (k) exceeds the predefined limit or (ii) active traffic flow routes when the shared or common edges (k) within the predefined limit. In one embodiment, the route solutions that exceed the pre-defined limit may be considered as the non-active traffic flow routes. The distributions generation module 212 generates distributions of the active traffic flow routes to avoid flash crowding and pollution concentration in a specific route on different days.

Figure 3:
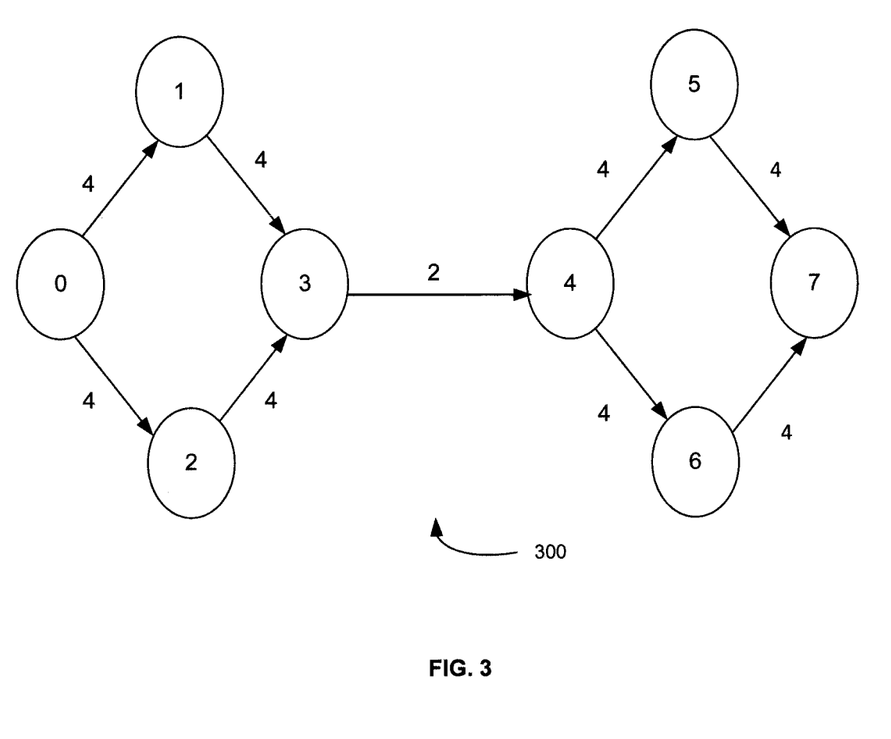
FIG. 3 is an exemplary view that illustrate a road network with intersections and edges/roads according to some embodiments herein.

FIG. 3 illustrates an exemplary view 300 of a road network with 8 intersections {0, 1, 2, 3, 4, 5, 6, 7} and 9 edges/roads 0-1, 0-2, 1-3, 2-3, 3-4, 4-5, 4-6, 5-7 and 6-7 according to some embodiments herein. The exemplary view 300 depicts that the Source S1 is 0 and the destination D1 is 7. In some embodiments, each edge/road associated with a value associated which represents the traffic flow capacity of each edge. Each edge within the route includes a pre-defined pollution level set by the server 108. The pollution level for the edges across the route decides the number of vehicles that are passing through the edges which further defines the traffic flow capacity of the edges. The traffic flow capacity of each edge within the road network are 0-1-"4"
0-2-"4"
1-3-"4"
2-3-"4"
3-4-"2"
4-5-"4"
4-6-"4"
5-7-"4" and
6-7-"4"

The server 108 identifies one or more possible routes that are optimized to the user 102 while traveling to the destination D1 from the source S1. In some embodiments, one or more route solutions between the S1 to the D1 are identified using a Breadth-first search algorithm. For the given road map in FIG. 3, the set of all identified route solutions are as follow:

Route 1: 0-1-3-4-5-7
Route 2: 0-2-3-4-5-7
Route 3: 0-1-3-4-6-7
Route 4: 0-2-3-4-6-7

The server 108 includes a pre-defined limit on common or shared edges between the two routes. For example, the road map includes limit as "1" which implies that at the most 1 edge can be shared or common between any two routes that would be part of the k-PMFA solution. The combination of the route solutions (1, 2, 3 and 4) are stored in the database 202 of the server 108. Further, the server 108 implements the Ford Fulkerson Algorithm (FFA) to calculate the maximum traffic flow through the road network. For example, the maximum flow (mf)=2 for this road network is due to the connecting edge 3-4. The FFA in the server 108 after computing the maximum traffic flow across the edges of the road network permutes 10 unique traffic flow permutations for each route. The 10 unique traffic flow permutations herein are as follows: {1, 1, 0, 0}, {1, 0, 1, 0}, {1, 0, 0, 1}, {0, 1, 1, 0}, {0, 1, 0, 1}, {0, 0, 1, 1}, {2, 0, 0, 0}, {0, 2, 0, 0}, {0, 0, 2, 0} and {0, 0, 0, 2}. In some embodiments, 1 or 2 indicates the traffic flow allowed across the routes and 0 indicates a non-active traffic flow zone. The server 108 includes the pre-defined limit for the number of edges the two route solutions should have in common. For example, if the pre-defined limit is 1, it implies that the number of edges the two route solutions are allowed to have in common is less than or equal to 1. The server 108 compares to determine the common edges between the two route solutions. For the comparison process route 1 is picked up initially and the comparison of route 1 with route 2 is done. The common or shared edges are less than or equal to 1 in this case. In some embodiments, the common edges are determined as 3-4 and 5-7 when comparing route 1 with route 2, the common edges are determined as 3-4 and 0-1 for the route 1 and 3 and the common edge is determined as 3-4 when comparing route 1 with route 4. In some embodiments, route 2 and route 3 are not taken into consideration due to the exceeding of the pre-defined limit of common edges between the two route solutions. Hence for routes 2 and 3, the traffic flow may remain "0". The traffic flow for routes 2 and 3 may remain "0" hence the following permutations gets invalidated: {1, 1, 0, 0}, {1, 0, 1, 0}, {0, 1, 1, 0}, {0, 1, 0, 1}, {0, 0, 1, 1}, {0, 2, 0, 0} and {0, 0, 2, 0}. The traffic flow solution set may be reduced from 10 to 3 i.e. {2, 0, 0, 0}, {0, 0, 0, 2} and {1, 0, 0, 1}. The server 108 generates distributions of the traffic flow across four routes in the manner calculated above and avoids flash crowding and pollution concentration in the specific route.

Figure 4A:
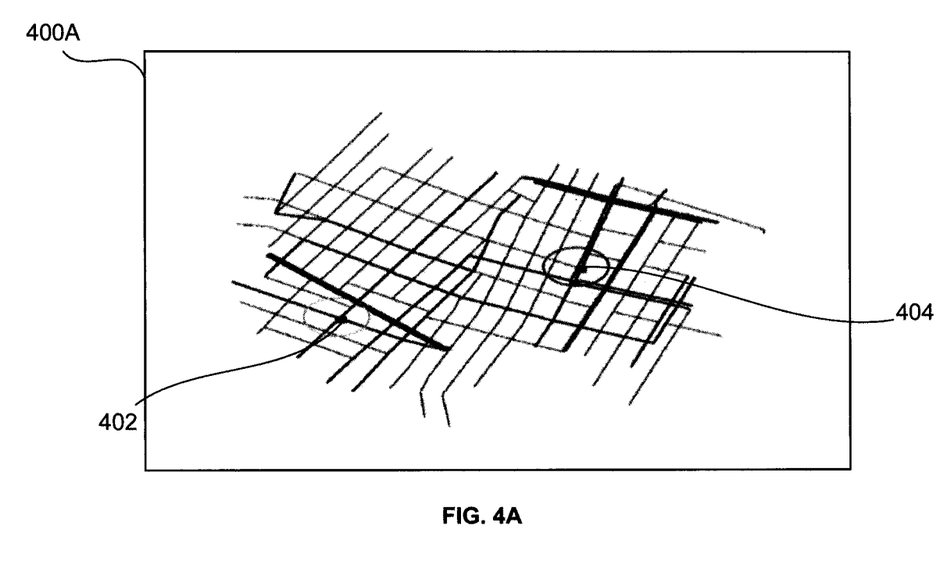
FIG. 4A illustrates an exemplary view of simulating a source node and a destination node in New York city map and providing a maximum traffic flow throughput according to some embodiments herein.

FIG. 4A illustrates an exemplary view of simulating a source node 402 and a destination node 404 in the New York city map and providing a maximum traffic flow throughput according to some embodiments herein. In FIG. 4A includes the source node 402 and the destination node 404 in the New York city map 400A. In some embodiments, the source node 402 and the destination node 404 are represented as a circular region with a radius of 100 meters. The New York city map 400A may be obtained using Open Street Maps (OSM). In some embodiments, the OSM is exported to a Simulation of Urban Mobility (SUMO) tool. The SUMO simulates traffic according to the size of a city, models individual vehicles and their interactions for car-following and lane-changing. In some embodiments, the SUMO also handles the dynamics of vehicles such as speed, acceleration, interaction with other vehicles such as overtaking, keeping a minimum distance, etc. In some embodiments, the SUMO allows to collect fuel consumption of the vehicles and pollutant emission values. In some embodiments, data relates to fuel consumption of the vehicles and pollutant emission values are provided from Handbook Emission Factors for Road Transport (HBEFA) database. The maximum traffic flow throughput between the source node and the destination node is obtained by considering two scenarios of metrics for a predefined limit (k) specified in the traffic flow routes determination module 210. In some embodiments, when the predefined limit is considered as the number of shared or common edges, following Table 1 that provides the variation of a number of flow solutions.

TABLE 1

| K | 20 | 40 | 60 | 80 | 100 |
|---|----|----|----|----|-----|
| No. of flow solutions | 1 | 37 | 112 | 174 | 174 |

In some embodiments, when the predefined limit is considered as normalized distance between the source node 402 and the destination node 404, a Table 2 that provides the variation of the number of flow solutions.

TABLE 2

| K | 0.2 | 0.4 | 0.6 | 0.8 | 1 |
|---|-----|-----|-----|-----|---|
| No. of flow solutions | 25 | 95 | 132 | 174 | 174 |

In some embodiments, the number of flow solutions increases as the distance between the source node 402 and the destination node 404 is increased. In some embodiments, as the common edges between the source node 402 and the destination node 404 is more, the number of flow solutions are more.

Figure 4B:
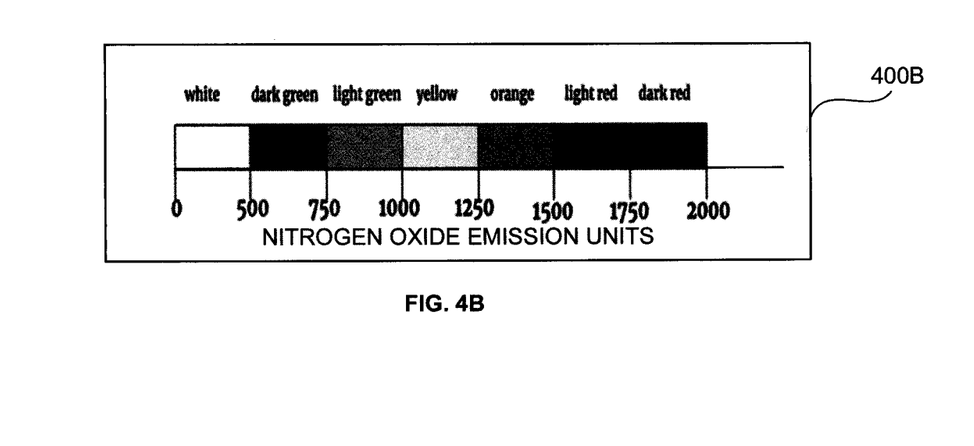
FIG. 4B illustrates an exemplary view of ranges representing concentrations of vehicular pollution according to some embodiments herein.

FIG. 4B illustrates an exemplary view of ranges representing concentrations of vehicular pollution according to some embodiments herein. In FIG. 4B represents the pollution level due to, for example, 1200 vehicles moving from the source node 402 to the destination node 404. In some embodiments, levels of pollution using a scale changing from dark green to dark red and light-green (as shown in the FIG. 4B) that represents lowest pollution density of 12.5% or 500 to 750 nitrogen oxide emission units. In some embodiments, the levels of pollution using the scale (as shown in the FIG. 4B) as yellow that represents the intermediate pollution density of 12.5% or 1000 to 1250 nitrogen oxide emission units. In some embodiments, the levels of pollution using the scale (as shown in the FIG. 4B) as orange represents the intermediate pollution density of 12.5% or 1250 to 1500 nitrogen oxide emission units. In some embodiments, the levels of pollution using the scale (as shown in the FIG. 4B) as light red and dark red represents the highest pollution density of 75% to 87.5% and 87.5% to 100% or 1500 to 1750 and 1750 to 2000 nitrogen oxide emission units.

Figure 4C:
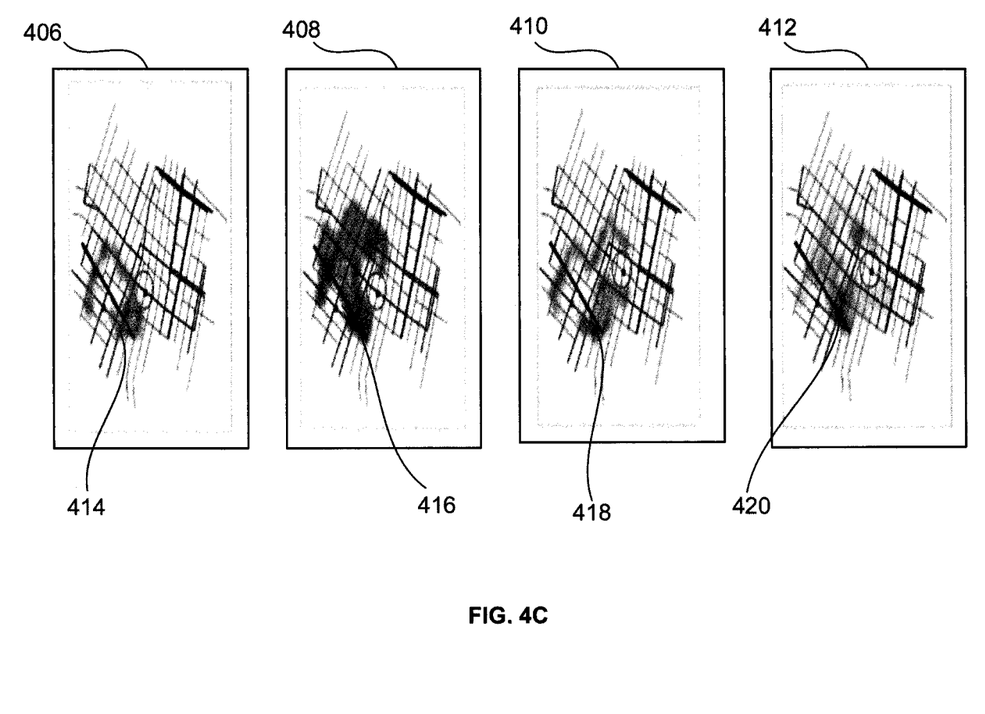
FIG. 4C illustrates an exemplary view of heat maps of concentrations of vehicular pollution between a source node and a destination node in New York city map according to some embodiments herein.

FIG. 4C illustrates an exemplary view of heat maps of concentrations of vehicular pollution between the source node 402 and the destination node 404 in the New York city map according to some embodiments herein. In FIG. 4C includes a heat map of concentrations of vehicular pollution between the source node 402 and the destination node 404 at a distance of 400 meters with traffic lights using Ford Fulkerson Algorithm (FFA) at 406, a heat map of concentrations of vehicular pollution between the source node and the destination node at a distance of 400 meters with traffic lights using the pollution control system 106 at 408, a heat map of concentrations of vehicular pollution between the source node and the destination node at a distance of 600 meters with traffic lights using Ford Fulkerson Algorithm (FFA) at 410, a heat map of concentrations of vehicular pollution between the source node and the destination node at a distance of 600 meters with traffic lights using the pollution control system 106 at 412.

In some embodiments, the heat map of concentrations of vehicular pollution between the source node 402 and the destination node 404 at a distance of 400 meters with traffic lights using Ford Fulkerson Algorithm (FFA) at 406 and the heat map of concentrations of vehicular pollution between the source node and the destination node at a distance of 600 meters with traffic lights using Ford Fulkerson Algorithm (FFA) at 410 have yellowish-green color for the majority of areas. The levels of pollution represent intermittent concentrations of vehicular pollution in the range of red as shown at 414 and at 418.

In some embodiments, the heat map of concentrations of vehicular pollution between the source node 402 and the destination node 404 at a distance of 400 meters with traffic lights using the server 108 at 408 and the a heat map of concentrations of vehicular pollution between the source node 402 and the destination node 404 at a distance of 600 meters with traffic lights using the server 108 at 412 have a majority of areas as dark-green with lower concentrations of yellowish-green or yellow. The levels of pollution represent a lower level of concentrations of vehicular pollution in the range of red as shown at 416 and at 420.

In some embodiments, the following Table 3 provides the average values of concentrations of vehicular pollution between the source node 402 and the destination node 404 at a distance of 400 meters and 600 meters for the Ford Fulkerson Algorithm (FFA) and the server 108 without

TABLE 3

| Distance | 400 meters | 600 meters |
|----------|------------|------------|
| FFA | 1305.27 | 1320.27 |
| Pollution Control system | 1175.56 | 1198.96 | traffic lights.

In some embodiments, the following Table 4 provides the average values of concentrations of vehicular pollution between the source node 402 and the destination node 404 at a distance of 400 meters and 600 meters for the Ford Fulkerson Algorithm (FFA) and the server 108 with traffic

TABLE 4

| Distance | 400 meters | 600 meters |
|----------|------------|------------|
| FFA | 1365.96 | 1395.70 |
| Pollution Control system | 1260.67 | 1298.45 | lights.

In some embodiments, the average values of concentrations of vehicular pollution between the source node 402 and the destination node 404 without traffic lights are less when compared to the average values of concentrations of vehicular pollution between the source node 402 and the destination node 404 with traffic lights.

In some embodiments, the following table 5 determines if the distance between the source node 402 and the destination node 404 increases then the number of route

TABLE 5

| Distance (meters) | 400 | 600 | 800 | 1000 | 1200 |
|-------------------|-----|-----|-----|------|------|
| No. of Route Solutions | 77 | 39 | 37 | 7 | 5 | solutions between the source node 402 and the destination node 404 decreases.

Figure 5:
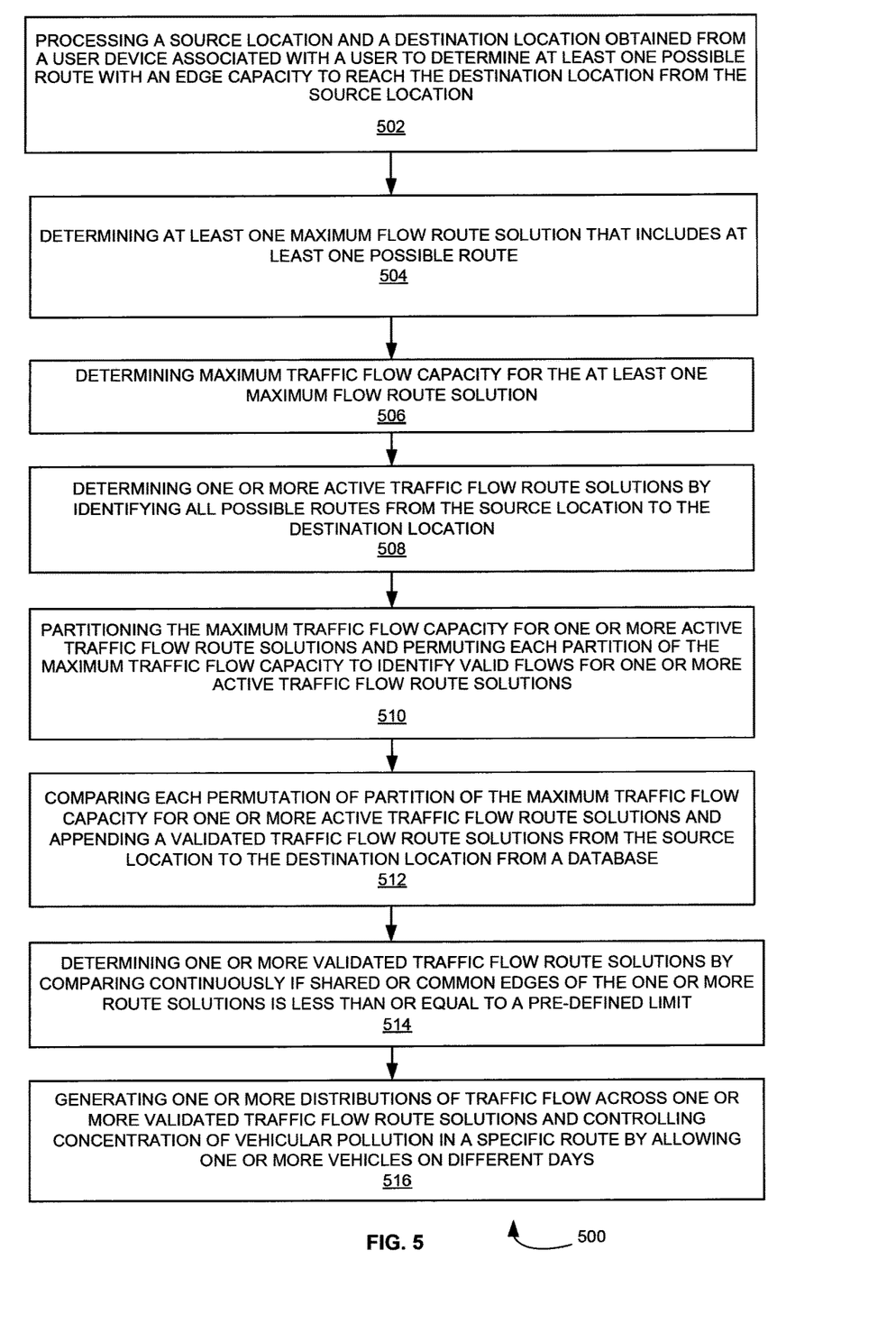
FIG. 5 is a flow diagram that illustrates a method for providing maximum traffic flow throughput and controlling vehicular pollution concentration according to some embodiments herein.

FIG. 5 is a flow diagram that illustrate a method 500 for providing maximum traffic flow throughput and controlling vehicular pollution concentration according to some embodiments herein. At step 502, the method 500 includes processing a source location and a destination location obtained from the user device 104 associated with the user 102 to determine at least one possible route with an edge capacity to reach the destination location from the source location. At step 504, the method 500 includes determining at least one maximum flow route solution that includes at least one possible route. At step 506, the method 500 includes determining maximum traffic flow capacity for the at least one maximum flow route solution. At step 508, the method 500 includes determining one or more active traffic flow route solutions by identifying all possible routes from the source location to the destination location. At step 510, the method 500 includes partitioning the maximum traffic flow capacity for the one or more active traffic flow route solutions and permuting each partition of the maximum traffic flow capacity to identify valid flows for the one or more active traffic flow route solutions. At step 512, the method 500 includes comparing each permutation of partition of the maximum traffic flow capacity for the one or more active traffic flow route solutions and appending a validated traffic flow route solution from the source location to the destination location to the database 200. At step 514, the method 500 includes determining one or more validated traffic flow route solutions by comparing continuously if shared or common edges of the one or more route solutions is less than or equal to a pre-defined limit. At step 516, the method 500 includes generating one or more distributions of traffic flow across the one or more validated traffic flow route solutions and controlling concentration of vehicular pollution in a specific route by allowing one or more vehicles on different days.

Figure 6:
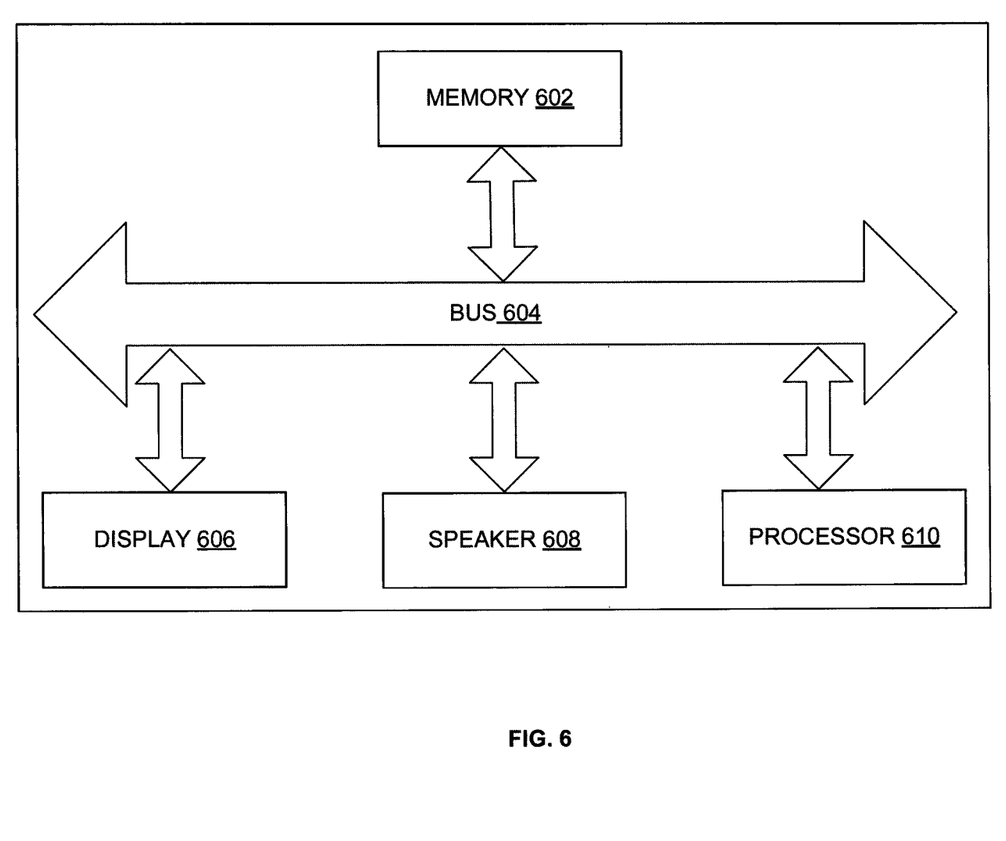
FIG. 6 illustrates an exploded view of a user device according to some embodiments herein.

FIG. 6 illustrates an exploded view of the user device 104 according to some embodiments herein. The user device 104 having a memory 602 having a set of computer instructions, a bus 604, a display 606, a speaker 608, and a processor 610 capable of processing a set of instructions to perform any one or more of the methodologies herein, according to an embodiment herein. The processor 610 may also enable digital content to be consumed in the form of a video for output via one or more displays 606 or audio for output via speaker and/or earphones 608. The processor 610 may also carry out the methods described herein and in accordance with the embodiments herein.

The embodiments herein may include a computer program product configured to include a pre-configured set of instructions, which when performed, can result in actions as stated in conjunction with the methods described above. In an example, the pre-configured set of instructions can be stored on a tangible non-transitory computer readable medium or a program storage device. In an example, the tangible non-transitory computer readable medium can be configured to include the set of instructions, which when performed by a device, can cause the device to perform acts similar to the ones described here. Embodiments herein may also include tangible and/or non-transitory computer-readable storage media for carrying or having computer executable instructions or data structures stored thereon.

Generally, program modules utilized herein include routines, programs, components, data structures, objects, and the functions inherent in the design of special-purpose processors, etc. that perform particular tasks or implement particular abstract data types. Computer executable instructions, associated data structures, and program modules represent examples of the program code means for executing steps of the methods disclosed herein. The particular sequence of such executable instructions or associated data structures represents examples of corresponding acts for implementing the functions described in such steps.

The embodiments herein can include both hardware and software elements. The embodiments that are implemented in software include but are not limited to, firmware, resident software, microcode, etc.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 7:
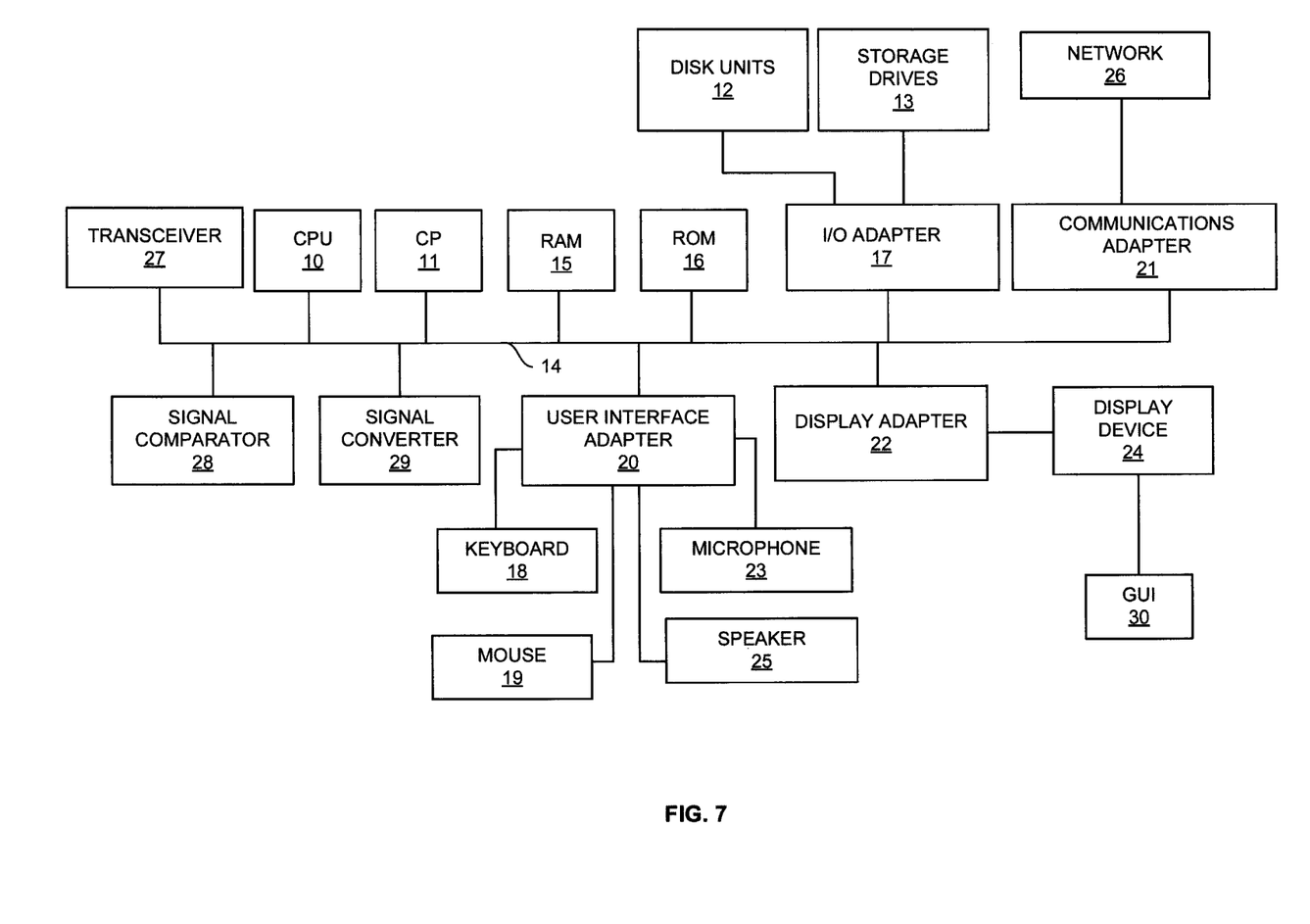
FIG. 7 is a block diagram of a schematic diagram of a device used in accordance with embodiments herein.

A representative hardware environment for practicing the embodiments herein is depicted in FIG. 7, with reference to FIGS. 1 through 6. This schematic drawing illustrates a hardware configuration of a server/computer system/user device in accordance with the embodiments herein. The user device includes at least one processing device 10 and a cryptographic processor 11. The special-purpose CPU 10 and the cryptographic processor (CP) 11 may be interconnected via system bus 14 to various devices such as a random access memory (RAM) 15, read-only memory (ROM) 16, and an input/output (I/O) adapter 17. The I/O adapter 17 can connect to peripheral devices, such as disk units 12 and tape drives 13, or other program storage devices that are readable by the system. The user device can read the inventive instructions on the program storage devices and follow these instructions to execute the methodology of the embodiments herein. The user device further includes a user interface adapter 20 that connects a keyboard 18, mouse 19, speaker 25, microphone 23, and/or other user interface devices such as a touch screen device (not shown) to the bus 14 to gather user input. Additionally, a communication adapter 21 connects the bus 14 to a data processing network 26, and a display adapter 22 connects the bus 14 to a display device 24, which provides a graphical user interface (GUI) 30 of the output data in accordance with the embodiments herein, or which may be embodied as an output device such as a monitor, printer, or transmitter, for example. Further, a transceiver 27, a signal comparator 28, and a signal converter 29 may be connected with the bus 14 for processing, transmission, receipt, comparison, and conversion of electric or electronic signals.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A method for providing maximum traffic flow throughput and controlling vehicular pollution concentration to enable the uniform distribution of the pollution and the reduction of the vehicular pollution concentration in a specific route, said method comprising:

determining at least one possible route by processing a source location and a destination location obtained from a user device associated with a user to reach the destination location from the source location, wherein the at least one possible route has at least one edge with an edge capacity;

determining, using a ford Fulkerson algorithm, at least one maximum flow route solution that comprises the at least one possible route;

determining, using the ford Fulkerson algorithm, maximum traffic flow capacity for the at least one maximum flow route solution;

determining a plurality of active traffic flow route solutions by identifying all possible routes from the source location to the destination location;

identifying valid flows for the plurality of active traffic flow route solutions by partitioning the maximum traffic flow capacity for the plurality of active traffic flow route solutions and permuting each partition of the maximum traffic flow capacity;

determining a plurality of validated traffic flow route solutions by comparing each permutation of partition of the maximum traffic flow capacity for the plurality of active traffic flow route solutions continuously if shared or common edges of the plurality of route solutions is less than or equal to a pre-defined limit and appending a validated traffic flow route solution from the source location to the destination location to a database;

and generating a plurality of distributions of traffic flow across the plurality of validated traffic flow route solutions to control vehicular pollution concentration and enable the uniform distribution of the pollution and the reduction of the vehicular pollution concentration in a specific route.

2. The method of claim 1, wherein at least one possible route solution is determined by (i) identifying at least one edge with a pre-defined capacity that is near to the source location and (ii) constructing a route from the source location to the destination location with the at least one edge.

3. The method of claim 1, wherein the maximum traffic flow capacity determined for at least one edge defines the plurality of vehicles acceptable in the at least one edge which determines a pollution level for the at least one edge.

4. The method of claim 1, further comprising measuring shared number of edges or shared distance between the source location and the destination location.

5. The method of claim 1, wherein the edge capacity is a value that defines traffic flow capacity of each edge.

6. One or more non-transitory computer-readable storage medium storing one or more sequence of instructions, which when executed by a processor, results in computation of maximum traffic flow throughput and resulting in a solution that controls vehicular pollution concentration to enable the uniform distribution of the pollution and the reduction of the vehicular pollution concentration in a specific route, the method comprising:

determining at least one possible route by processing a source location and a destination location obtained from a user device associated with a user to reach the destination location from the source location, wherein the at least one possible route has at least one edge with an edge capacity;

determining, using a ford Fulkerson algorithm, at least one maximum flow route solution that comprises the at least one possible route;

determining, using the ford Fulkerson algorithm, maximum traffic flow capacity for the at least one maximum flow route solution;

identifying valid flows for the plurality of active traffic flow route solutions by partitioning the maximum traffic flow capacity for the plurality of active traffic flow route solutions and permuting each partition of the maximum traffic flow capacity;

determining a plurality of validated traffic flow route solutions by comparing each permutation of partition of the maximum traffic flow capacity for the plurality of active traffic flow route solutions continuously if shared or common edges of the plurality of route solutions is less than or equal to a pre-defined limit and appending a validated traffic flow route solution from the source location to the destination location to a database;

and generating a plurality of distributions of traffic flow across the plurality of validated traffic flow route solutions to control vehicular pollution concentration and enable the uniform distribution of the pollution and the reduction of the vehicular pollution concentration in a specific route.

7. The one or more non-transitory computer-readable storage medium storing the one or more sequence of instructions of claim 6, further causes measuring shared number of edges or shared distance between the source location and the destination location.

8. A system for providing maximum traffic flow throughput and controlling vehicular pollution concentration to enable the uniform distribution of the pollution and the reduction of the vehicular pollution concentration in a specific route, said system comprising:

a server that is communicatively coupled with a user device associated with a user, wherein the server comprises a memory that stores a set of instructions; and a processor that executes the set of instructions and is configured to, determine at least one possible route by processing a source location and a destination location obtained from a user device associated with a user to reach the destination location from the source location, wherein the at least one possible route has at least one edge with an edge capacity;

determine, using a ford Fulkerson algorithm, at least one maximum flow route solution that comprises the at least one possible route;

determine, using the ford Fulkerson algorithm, maximum traffic flow capacity for the at least one maximum flow route solution;

determine a plurality of active traffic flow route solutions by identifying all possible routes from the source location to the destination location;

identify valid flows for the plurality of active traffic flow route solutions by partitioning the maximum traffic flow capacity for the plurality of active traffic flow route solutions and permuting each partition of the maximum traffic flow capacity;

determine a plurality of validated traffic flow route solutions by comparing each permutation of partition of the maximum traffic flow capacity for the plurality of active traffic flow route solutions continuously if shared or common edges of the plurality of route solutions is less than or equal to a pre-defined limit and appending a validated traffic flow route solution from the source location to the destination location to a database;

and generate a plurality of distributions of traffic flow across the plurality of validated traffic flow route solutions to control vehicular pollution concentration and enable the uniform distribution of the pollution and the reduction of the vehicular pollution concentration in a specific route.

9. The system of claim 8, wherein the at least one possible route solution is determined by (i) identifying at least one edge with a pre-defined capacity that is near to the source location, (ii) constructing a route from the source location to the destination location with the at least one edge.

10. The system of claim 8, wherein the maximum traffic flow capacity determined for at least one edge defines the plurality of vehicles acceptable in the at least one edge which determines a pollution level for the at least one edge.

11. The system of claim 8, wherein the processor configured to measure shared number of edges or shared distance between the source location and the destination location.

* * * * *